(12) United States Patent
Marshall

(10) Patent No.: US 6,602,273 B2
(45) Date of Patent: Aug. 5, 2003

(54) FILTER DELIVERY DEVICE

(75) Inventor: Peter Marshall, Newburyport, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/964,073

(22) Filed: Sep. 26, 2001

(65) Prior Publication Data

US 2002/0032461 A1 Mar. 14, 2002

Related U.S. Application Data

(63) Continuation of application No. 09/404,115, filed on Sep. 23, 1999, now Pat. No. 6,328,755.
(60) Provisional application No. 60/101,638, filed on Sep. 24, 1998.

(51) Int. Cl.[7] .............................................. A61M 29/00
(52) U.S. Cl. ...................................................... 606/200
(58) Field of Search ................................ 606/200, 113, 606/114, 127; 604/104, 165.01, 165.02

(56) References Cited

U.S. PATENT DOCUMENTS

| | | | |
|---|---|---|---|
| 3,952,747 A | 4/1976 | Kimmell, Jr. ............... 128/303 |
| 4,425,908 A | 1/1984 | Simon .......................... 128/1 |
| 4,643,184 A | * 2/1987 | Mobin-Uddin .............. 604/104 |
| 4,832,055 A | 5/1989 | Palestrant ................... 128/899 |
| 5,147,379 A | 9/1992 | Sabbaghian et al. ........ 606/206 |
| 5,300,086 A | 4/1994 | Gory et al. .................. 606/200 |
| 5,324,304 A | 6/1994 | Rasmussen .................. 606/200 |
| 5,370,657 A | 12/1994 | Irie ............................. 606/200 |
| 5,413,586 A | 5/1995 | Dibie et al. ................. 606/200 |
| 5,415,630 A | 5/1995 | Gory et al. ................... 604/53 |
| 5,601,595 A | 2/1997 | Smith .......................... 606/200 |
| 5,634,942 A | 6/1997 | Chevillon et al. ............. 623/1 |
| 5,649,953 A | 7/1997 | Lefebvre ..................... 606/200 |
| 5,681,347 A | * 10/1997 | Cathcart et al. ............ 606/200 |
| 5,709,704 A | 1/1998 | Nott et al. .................. 606/200 |
| 5,810,874 A | 9/1998 | Lefebvre ..................... 606/200 |
| 5,814,064 A | 9/1998 | Daniel et al. ............... 606/200 |
| 5,836,968 A | 11/1998 | Simon et al. ................ 606/200 |
| 5,947,995 A | 9/1999 | Samuels ...................... 606/200 |

* cited by examiner

Primary Examiner—Cary E. O'Connor
(74) Attorney, Agent, or Firm—Crompton, Seager & Tufte LLC

(57) ABSTRACT

Devices and methods for delivering a thrombus filter are disclosed. A system in accordance with the present invention includes an elongate shaft having a proximal end, a distal end, and a lumen extending therethrough, a hub disposed about the shaft proximate the proximal end thereof, a pull wire having a proximal end, a distal end, and middle portion, the proximal end of the pull wire being fixed to the hub and the middle portion of the pull wire being disposed within the lumen of the shaft, the distal end of the pull wire being fixed to a capsule disposed about a portion of the thrombus filter, and an elongate rod slidingly disposed within the lumen of the shaft.

18 Claims, 2 Drawing Sheets

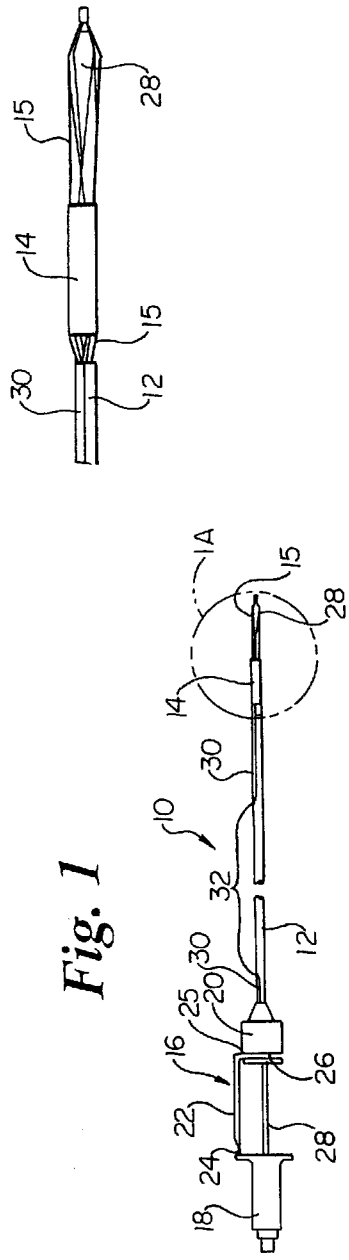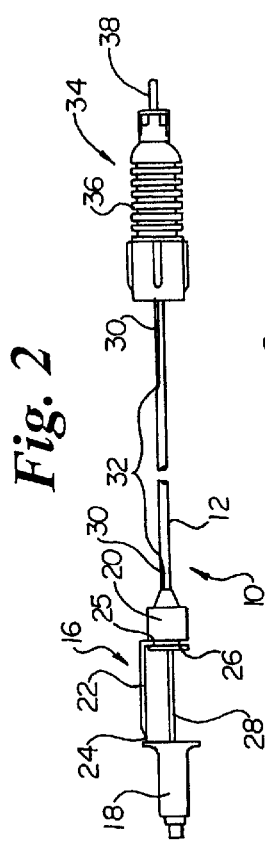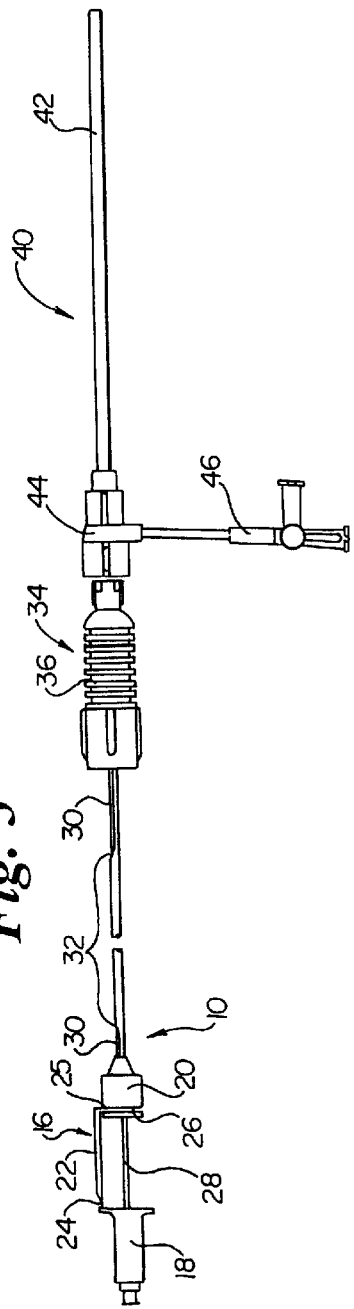

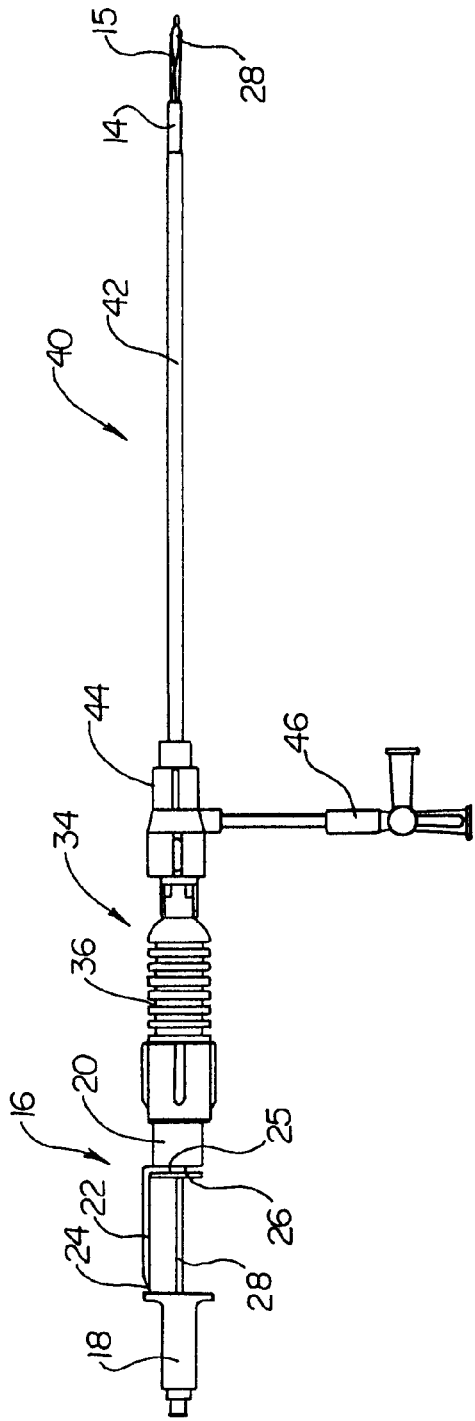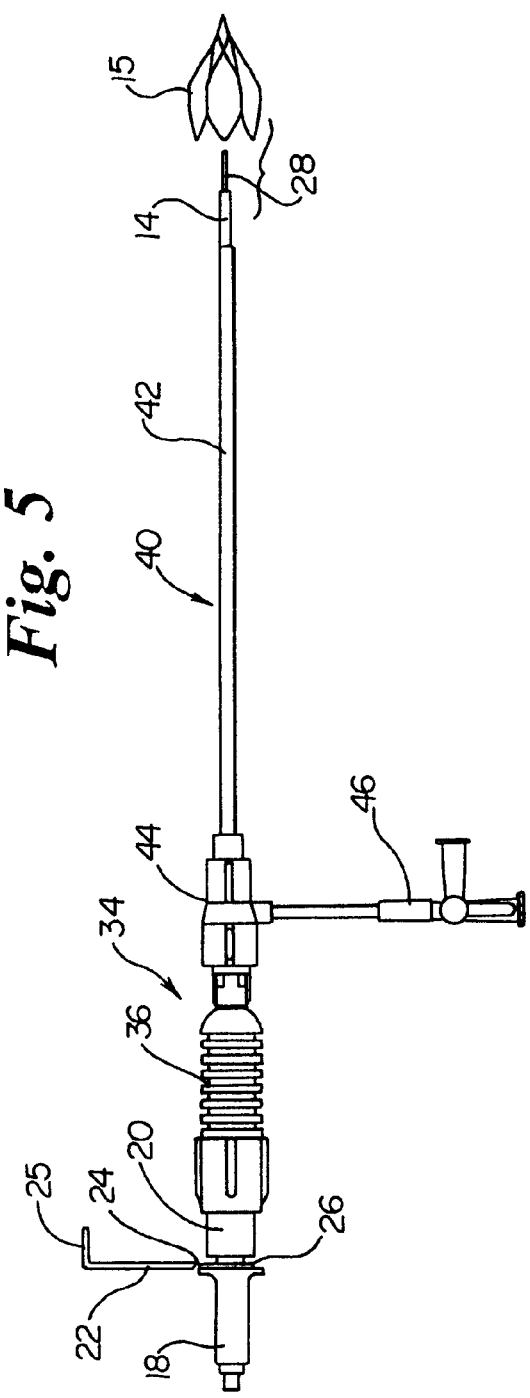

FILTER DELIVERY DEVICE

CROSS REFERENCE TO RELATED APPLICATION

This is a continuation of application Ser. No. 09/404,115 filed on Sep. 23, 1999, now U.S. Pat. No. 6,328,755.

The present application claims the benefit of U.S. Provisional Application Serial No. 60/101,638, filed Sep. 24, 1998.

BACKGROUND OF THE INVENTION

The present invention pertains to the field of intra vena cava filters. In particular, the present invention pertains to the delivery of intra vena cava filters.

Intra vena cava filters are implanted in patients at risk for blood clotting. One such filter is disclosed by Nott et al., in U.S. Pat. No. 5,709,704, which issued Jan. 20, 1998 and is entitled "Blood Clot Filtering".

SUMMARY OF THE INVENTION

The present invention pertains to a delivery device for a self-expanding vena cava filter such as the one disclosed by Nott et al. in U.S. Pat. No. 5,709,704 which is incorporated herein by reference. The filter is preferably formed from super-elastic NiTi alloy wire with anchoring hooks circumferentially disclosed on the filter. The filter hooks have sharp ends to engage the intima wall of the vena cava to stabilize the filter therein. The delivery device in accordance with the present invention includes a protective capsule into which the filter is placed such that the hooks are disposed within the capsule for transport to a filter deployment site.

BRIEF DESCRIPTION OF THE DRAWINGS

FIG. 1 is a side view of a catheter in accordance with the present invention having a filter capsule disposed at its distal end;

FIG. 2 is a view of the catheter of FIG. 1, wherein the distal end is disposed within a cheater;

FIG. 3 is a view of the catheter and cheater of FIG. 2, wherein the cheater is connected to an introducer sheath;

FIG. 4 is a view of the catheter, cheater and introducer sheath of FIG. 3, wherein the capsule has been advanced through the introducer sheath; and FIG. 5 is a view of the catheter, cheater and introducer sheath of FIG. 4 and a deployed filter.

DETAILED DESCRIPTION OF THE INVENTION

Referring now to the drawings wherein like reference numerals refer to like elements throughout the several views, FIG. 1 is a side view of the preferred embodiment of a filter delivery catheter 10 in accordance with the present invention. Catheter 10 includes an elongate catheter shaft 12 having a proximal and distal end. A capsule 14 is disposed at the distal end of shaft 12. For purposes of illustration, a filter 15, such as that disclosed by Nott et al. in U.S. Pat. No. 5,709,704, is shown disposed within capsule 14. Not visible are the hooks circumferentially disposed on filter 15 which engage the intima wall of the vena cava when filter 15 is disposed therein. Capsule 14 is thus preferably sufficiently durable to resist puncture by the hooks. The materials which could be used to form capsule 14 include, among others, metals, such as the form of stainless steel hypotube, and high density polymer or composite materials. The materials can also be radiopaque to improve visibility under fluoroscopy.

A handle assembly 16 is disposed at the proximal end of shaft 12. Handle assembly 16 includes a handle 18 and a hub 20 connected to shaft 12. Disposed between handle 18 and hub 20 is a locking member 22 pivotally connected to handle 18 by hinge 24. The end of locking member 22, opposite hinge 24, includes a portion disposed generally perpendicularly to the length of catheter 10. Portion 25 is preferably configured to friction fit into a slot 26 within hub 20. An elongate rod 28 extends distally from handle 18, and slidably through hub 20, shaft 12 and capsule 14 into filter 15. A capsule pull wire having a proximal end and a distal end preferably extends through an elongate lumen 32 disposed through a portion of shaft 12. The proximal end of pull wire 30 is preferably connected to hub 20 and the distal end is connected to capsule 14. FIG. 1A is a detailed view of the distal end of shaft 20, capsule 14 and filter 15 taken from FIG. 1.

FIG. 2 is a side view of catheter 10, wherein capsule 14 and filter 15 have been inserted into a cheater 34. Cheater 34 includes a handle 36 and a coupling 38.

FIG. 3 is a view of the catheter and cheater of FIG. 2, wherein coupling 38 has been inserted into a complimentary coupling 44 of an introducer sheath 40. In addition to coupling 44, introducer sheath includes an elongate shaft tube 42. Coupling 44 can also serve as a manifold to which a further coupling 46 can be connected for infusion of contrast medium, saline or other fluids into a patient's vasculature.

FIG. 4 is a side view of handle assembly 16 of catheter 10, cheater 34 and introducer sheath 40. As shown in FIG. 4, shaft 12 of catheter 10 has been advanced through handle 36 and introducer shaft 42 such that hub 20 is disposed adjacent cheater 34 and filter 15 and capsule 14 are disposed distally of the distal end of shaft 42.

FIG. 5 is a side view of handle 18 of catheter 10, cheater 34 and delivery sheath 40. Locking member 22 of handle 16 has been pivoted about hinge 24 such that portion 25 has been removed from slot 26. This allows, as shown in FIG. 5, handle 18 to moved distally toward hub 20 such that shaft 28 is shifted distally relative to capsule 14 while wire 30 retains capsule 14 in position relative to hub 20. Shaft 28 thus advanced distally pushes filter 15 out of capsule 14. Alternately handle 36 and hub 20 could be pulled proximally to pull capsule 14 off of filter 15. Once filter 15 is unconstrained by capsule 14, it assumes its expanded shape in the vena cava.

In use, it can be appreciated that the distal end of shaft 42 of delivery sheath 40 can be advanced to the desired placement location of filter 15 in the vena cava. Shaft 42 can be advanced by way of a femoral, brachial, or jugular vein approach. Capsule 14 and filter 15 can be advanced through shaft 42 as shown in FIG. 4. Then shaft 28 is advanced to deploy filter 15 into the vena cava.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. An intravascular filtering device, comprising:
   an elongate member having a proximal end, a distal end, and a lumen extending therethrough;
   an elongate rod slidably disposed relative to the elongate member, the rod having a proximal end and a distal end;
   a locking member coupled to the elongate rod, the locking member being adapted and configured to fix the position of the rod relative to the elongate member;

a capsule disposed at the distal end of the elongate member, the capsule including a proximal opening, a distal opening, and a lumen extending therebetween;

a filter having a proximal portion and a distal portion, wherein at least the proximal portion is disposed within the capsule; and a handle disposed at the proximal end of the rod, wherein the locking member is coupled to the handle by a hinge and wherein the locking member is adapted to shift between a first position and a second position about the hinge, the first position essentially preventing movement of the rod relative to the elongate member and the second position allowing movement of the rod relative to the elongate member.

2. The filtering device in accordance with claim 1, wherein the filter includes one or more anchors on the proximal portion.

3. An intravascular filtering device, comprising:

an elongate tube having a proximal end, a distal end, and a lumen extending therethrough;

an elongate rod slidably disposed within the tube, the rod having a proximal end and a distal end;

means for controlling the position of the rod relative to the tube;

a capsule disposed at the distal end of the tube, the capsule including a proximal opening, a distal opening, and a lumen extending therebetween;

a filter having a proximal portion and a distal portion, wherein at least the proximal portion is disposed within the capsule, the proximal portion of the filter including one or more anchors; and a locking member having a hinge.

4. The filtering device in accordance with claim 3, wherein means for controlling the position of the rod relative to the tube includes a handle disposed at the proximal end of the rod.

5. The filtering device in accordance with claim 4, wherein the hinge connects the locking member to the handle.

6. The filtering device in accordance with claim 3, wherein means for means for controlling the position of the rod relative to the tube includes a pull wire coupled to the capsule.

7. A method of filtering embolic debris from a body lumen, comprising the steps of:

providing a filtering device, the filtering device including an elongate tubular member, an elongate rod slidably disposed within the tubular member, a handle disposed at a proximal end of the rod, a capsule disposed at a distal end of the tubular member, the capsule including a proximal opening, a distal opening, and a lumen extending therebetween, and a filter having a proximal portion and a distal portion, wherein at least the proximal portion is disposed within the capsule;

providing an introducer sheath having a proximal coupling and a distal shaft;

disposing the distal shaft within a body orifice;

attaching the filtering device to the proximal coupling; and advancing the filter through the introducer sheath and into the body orifice.

8. The method in accordance with claim 7, wherein the step of attaching the filtering device to the proximal coupling includes inserting the capsule into a cheater and attaching the cheater to the proximal coupling.

9. The method in accordance with claim 7, wherein the introducer sheath further comprises a second coupling, and further comprising the step of infusing a fluid through the second coupling and into the body orifice.

10. The method in accordance with claim 7, wherein the step of advancing the filter through the introducer sheath and into the body orifice includes distally moving the handle.

11. The method in accordance with claim 7, wherein the filter is adapted to shift between a collapsed configuration and an expanded configuration, and wherein the step of advancing the filter through the introducer sheath and into the body orifice includes the step of shifting the filter to the expanded configuration.

12. The method in accordance with claim 11, wherein the filter includes one or-more anchors, and wherein the step of shifting the filter to the expanded configuration includes anchoring the filter within the body orifice with the anchors.

13. An intravascular filtering device, comprising:

an elongate tubular member having a proximal end, a distal end, and a lumen extending therethrough;

an elongate rod slidably disposed within the tubular member, the rod having a proximal end and a distal end;

a handle disposed at the proximal end of the rod;

a capsule disposed at the distal end of the tubular member, the capsule including a proximal opening, a distal opening, and a lumen extending therebetween;

a filter having a proximal portion and a distal portion, wherein at least the proximal portion is disposed within the capsule;

a cheater attached to the capsule, the cheater having a distal coupling; and an introducer sheath attached to the cheater at the distal coupling.

14. An intravascular filtering device, comprising:

an elongate tube having a proximal end, a distal end, and a lumen extending therethrough;

an elongate rod slidably disposed within the tube, the rod having a proximal end and a distal end;

a hub coupled to the tube near the proximal end thereof, a capsule disposed at the distal end of the tubular member, the capsule including a proximal opening, a distal opening, and a lumen extending therebetween;

a pull wire having a proximal end and a distal end, the proximal end being coupled to the hub and the distal end being coupled to the capsule;

a filter detachably connected to the capsule, the filter including one or more anchors;

a handle coupled to the proximal end of the rod; and and a locking member having a first end and a second end, the first end being connected to the handle by a hinge.

15. The filtering device in accordance with claim 14, wherein the filter includes a proximal portion and a distal portion, and wherein the anchors are disposed at the proximal portion.

16. The filtering device in accordance with claim 14, wherein the locking member is configured to shift between a first position and a second position.

17. The filtering device in accordance with claim 16, wherein the first position includes the second end of the handle being disposed proximate the hub such that the locking member secures the position of the handle relative to the hub.

18. The filtering device in accordance with claim 16, wherein the second position includes the second end of the handle being disposed a distance away from the hub so as to allow movement of the handle relative to the hub.

* * * * *